United States Patent [19]

Knight et al.

[11] 4,170,661

[45] Oct. 9, 1979

[54] METHOD OF TREATING INTRAOCULAR LENS AND THE LIKE

[75] Inventors: Patricia M. Knight, Costa Mesa; William J. Link, Irvine, both of Calif.

[73] Assignee: American Hospital Supply Corporation, Evanston, Ill.

[21] Appl. No.: 855,962

[22] Filed: Nov. 30, 1977

[51] Int. Cl.$^2$ ............................ A61F 9/00; B05D 3/00; B05D 1/18

[52] U.S. Cl. ................................................ 427/2; 3/13; 427/164; 427/444

[58] Field of Search ................ 427/2, 164, 444; 3/13; 128/303 R, 321, 322, 323, 324

[56] References Cited

U.S. PATENT DOCUMENTS

| | | | |
|---|---|---|---|
| 2,688,139 | 9/1954 | Jardon | 3/13 |
| 3,711,870 | 1/1973 | Deitrick | 3/13 |
| 3,906,551 | 9/1975 | Otter | 3/13 |
| 3,996,627 | 12/1976 | Deeg et al. | 3/13 |

OTHER PUBLICATIONS

Newsweek, "New Lens for Cataracts", Jun. 30, 1975, p. 45.
Kaufman et al., "Endothelial Damage from Intraocular Lens Insertion", Inv. Ophth., vol. 15 (1976) pp. 996-1000.
Kaufman et al., "Prevention of Endothelial Damage from Intraocular Lens Insertion", Tr. Am. Acad. Ophth. & Otol., vol. 83 (1977) pp. 204-212.
Kaufman et al., "Pathology of the Corneal Endothelium", Inv. Ophth. Visual Sci., vol. 16 (1977) pp. 265-268.
Fechner, "Methyl Cellulose in Lens Implantation", J. Am. Intraocular Implant Soc., vol. 3 (1977), pp. 180-181.
Kaufman et al., "Corneal Endothelium Damage with Intraocular Lenses: Contact Adhesion Between Surgical Materials and Tissue", Science, vol. 198 (1977), pp. 525-527.

*Primary Examiner*—James R. Hoffman
*Attorney, Agent, or Firm*—Larry N. Barger

[57] ABSTRACT

A method of treating an intraocular lens or ophthalmic surgical tool with a water-soluble adherent film forming material, such as polyvinyl alcohol, in a liquid media after which the liquid media is evaporatively removed to provide a dehydrated coating that is both water-soluble and liquid swellable. The device is packaged and sterilized, such as by ethylene oxide, and supplied to the ophthalmologist. Immediately prior to its use in surgery, the ophthalmologist rehydrates the coating by submerging in a sterile aqueous bath causing the coating to swell into a soft sluffable cushion for protecting a corneal endothelium during both static touch contact and dynamic sliding contact with the coated lens or tool.

23 Claims, 6 Drawing Figures

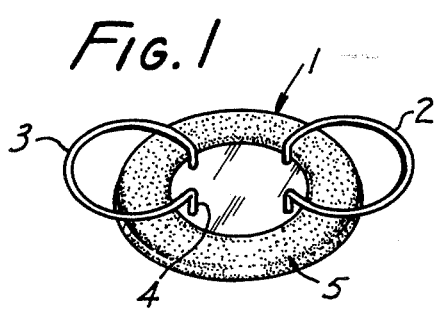
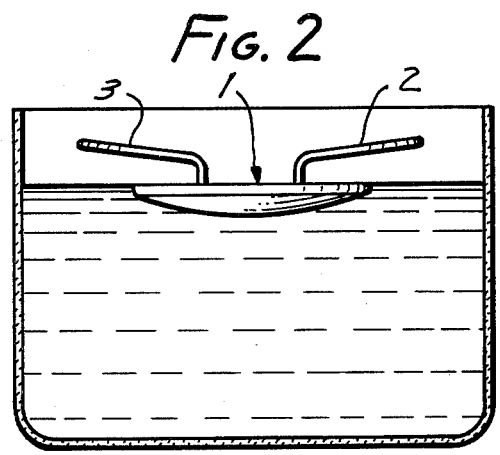
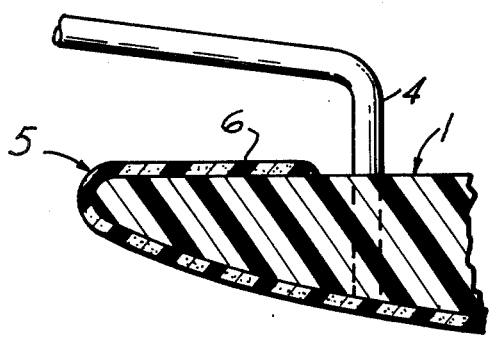
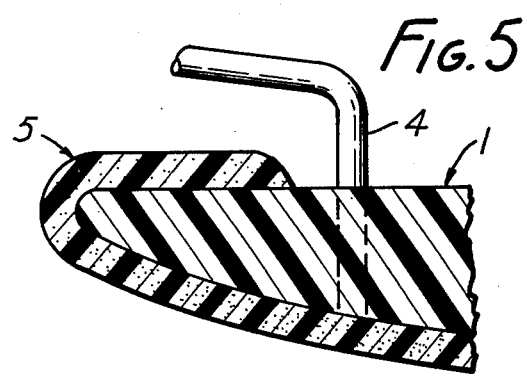
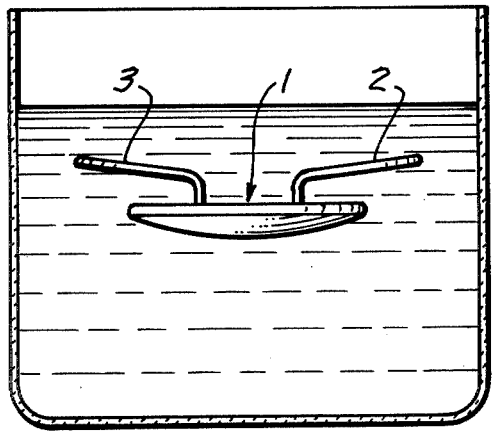
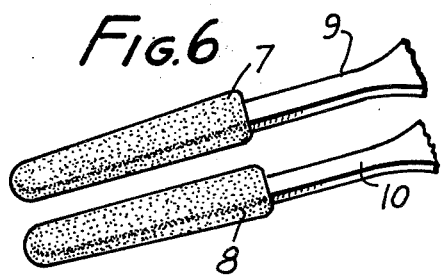

METHOD OF TREATING INTRAOCULAR LENS AND THE LIKE

BACKGROUND

H. E. Kaufman, M.D. and others have identified a serious problem in intraocular lens implantation dealing with the destruction of corneal endothelium cells. It is generally recognized that the corneal endothelium will not regenerate itself and is extremely important as a boundary layer between the outer layers of the cornea and the aqueous humor in the anterior chamber of the eye. The corneal endothelium is extremely delicate in that the endothelium is only one cell thick.

The intraocular lenses commonly implanted are of a polymethylmethacrylate (PMMA) material which has excellent optical qualities and biocompatibility once it is surgically implanted. Once implanted the location of the intraocular lens is such that, when in its proper position, it does not contact or damage the corneal endothelium. There is a continuous washing or flushing of the anterior chamber including the corneal endothelium.

During surgical implantation of an intraocular lens, the cornea is surgically opened and the intraocular lens manipulated in place frequently with retention loops placed behind the iris. Sometimes the manipulation includes puncturing the iris with a miniature safety pin type prong or clip to attach the lens to the iris.

During the surgical implantation and manipulation, it frequently happens that the corneal endothelium is staticly touched or dynamically scraped with a PMMA lens or surgical tool. Dr. Kaufman and others have recognized the problem of corneal endothelium damage during surgery and have proposed dipping the lens in a coating of methylcellulose (MC) or polyvinylpyrrolidone (PVP). These coatings were applied by the ophthalmologist immediately prior to surgery as a wet and slippery coating on the lenses.

Dipping of the lenses in MC or PVP is useful to protect the corneal endothelium. However, because of a fast dissolution rate of these polymers and the difficulty of placing a controlled amount of such polymers on the lenses, the extent and length of the protection is uncontrollable. Because of the wet and slippery nature of the lenses dipped during surgery, the lenses are difficult to handle and a portion of the coating may drip off. In addition, MC and PVP solutions must be sterilized prior to dipping. Subsequently, Dr. Fechner (citation below) published the results of a repeat of the Dr. Kaufman et al experiments with a complicated attempt to sterilize methylcellulose in very small quantities to keep it from coalescing and changing viscosity. In practice, the complicated procedure described for the sterile methylcellulose coating is not feasible for the ophthalmologist to perform in the operating room.

The background publications by Dr. Kaufman et al explaining the corneal endothelium damage during intraocular lens implantation and experiments with methylcellulose and polyvinylpyrrolidone coating are as follows.

Kaufman, H. E. and J. I. Katz, "Endothelial Damage From Intraocular Lens Insertion," Inv. Ophth., Vol. 15(12), Dec. 1976, p. 996-1000

Kaufman, H. E., Jeffry Katz, et al, "Prevention of Endothelial Damage From Intraocular Lens Insertion," Tr. Am. Acad. Ophth. & Otol., Vol. 83, Mar-Apr. 1977, p. 204-212

Kaufman, H. E. and J. I. Katz, "Pathology of the Corneal Endothelium," Inv. Ophth. Visual Sci., Vol. 16(4), April 1977, p. 265-268

Fechner, P. U., "Methylcellulose In Lens Implantation," Jour. Amer. Intraocular Implant Society, Vol. 3(3 & 4), July-October 1977, p. 180-181

Kaufman, H. E., Jeffrey Katz, et al, "Corneal Endothelium Damage with Intraocular Lenses: Contact Adhesion Between Surgical Materials and Tissue," Science, Vol. 198(4316), Nov. 4, 1977, p. 525-527.

SUMMARY OF THE INVENTION

The present invention includes a method of precoating an intraocular lens or surgical tool with a liquid media containing a water-soluble adherent film forming material, such as polyvinyl alcohol, and then removing the liquid media by evaporation. The lens or tool with its firmly adherent dry coating is then packaged and sterilized, such as by ethylene oxide.

Immediately prior to its use in surgery, the ophthalmologist rehydrates the lens or tool simply by dipping it into a sterile liquid of normal saline or a balanced salt solution. This swells the coating into a spongey sluffable protective layer that protects the corneal endothelium during static touch contact as well as dynamic sliding contact with the coated lens or surgical tool. After implantation, the continual flushing action of the anterior chamber of the eye removes the coating from the lens in a period of several hours.

The present application deals with the method of treating the intraocular lens or surgical tool. A related application by the same inventors is entitled "Intraocular Lens And Surgical Tool For Implanting Same," filed Nov. 30, 1977, Ser. No. 855,961, relates to the coated lens and surgical tools themselves.

THE DRAWINGS

FIG. 1 is a rear prospective view of an intraocular lens which has been coated according to such process;

FIG. 2 is a schematic view showing the dip coating step of the process;

FIG. 3 is an enlarged sectional view of the lens after its coating has been dehydrated;

FIG. 4 is a schematic view showing the lens submerged in a liquid during the rehydrating step;

FIG. 5 is an enlarged sectional view showing the swollen coating in rehydrated state; and FIG. 6 is a prospective view of an ophthalmic surgery forceps with the rehydrated coating on such tip sections.

DETAILED DESCRIPTION

FIG. 1 shows a typical intraocular lens with an optical section shown generally at 1 with a pair of looped sections 2 and 3 that are joined to the optical section by shank portions, such as at 4. The optical section 1 has a coating 5 that covers its entire front surface, its outer edge, and a circumferential band 6 at its rear portion. If desired, circumferential band 6 could be eliminated with the coating covering only the optical section's front and peripheral edge.

It is preferable that loop sections 2 and 3 not be coated, because such coating tends to bridge the loop sections and introduce more coating material into the eye than is actually needed. The front and peripheral edges of the optical section 1 are those areas of the intraocular lens most likely to contact the corneal endothelium.

The method of making the intraocular lens of this invention includes forming the lens, and then dipping only that portion intended to be coated in a water solution of the water-soluble material. Excellent results have been obtained by dip coating the lens in a 5% aqueous solution of polyvinyl alcohol. Although 5% concentration of polyvinyl alcohol (PVA) is used, the concentration could be varied from 1% to 60% depending upon the thickness of coating desired and the number of dips. Preferably two dip coats are applied with an air drying step between the coats.

Once the complete coating has been applied, the water or other liquid media is removed by evaporative drying. A substantially dry very adherent film remains on the lens. It is important that the coating material be a good film former and not "bead up" to expose certain uncoated areas of the lens. Polyvinyl alcohol is an excellent film former.

The lens as shown in FIG. 3 with its substantially dry coating is then packaged and subjected to sterilization, such as by ethylene oxide. Because there are many different package designs that could be used, it is not believed necessary to schematically show a package nor to illustrate the equipment for sterilizing such packaged lens.

The lens in its packaged sterilized form with its dehydrated coating is supplied to the ophthalmologist. Immediately prior to insertion of the lens, the ophthalmologist rehydrates the lens by submerging it in a sterile liquid, such as normal saline or a balanced salt solution. After this rehydration step, which takes approximately 1 to 10 minutes at room temperature, the coated lens has a swollen cushion as shown in FIG. 5. Good results have been obtained with rehydration for 5 minutes. It is estimated that the hydrated coating has a thickness of approximately 10 to 1000 microns, while the dehydrated coating has a thickness of approximately 5 to 300 microns.

Once the intraocular lens has been surgically implanted, the continuous biological flushing action of the aqueous humor in the anterior chamber dissolves the coating from the lens. The coating is believed to eventually be excreted through the urine.

FIG. 6 shows a rehydrated coating 7 and 8 on tip sections 9 and 10 of an ophthalmic surgery tool that is likely to contact the corneal endothelium. An example of such tool is a Hirshman spatula.

Once the intraocular lens or surgical tool has been rehydrated as explained above, it is important that a rehydrated film does not quickly dehydrate when exposed to air. It has been found that the polyvinyl alcohol in rehydrated form will maintain its rehydrated state in a time range of 20 minutes 1½ hours. In a typical intraocular lens implant, the cornea is surgically opened for about ½ hour. Also during the surgery, the coated lens or tool is flushed with liquid and also in contact with the aqueous humor of the anterior chamber which tends to delay a dehydration of the coating by air drying.

The polyvinyl alcohol coating is much superior to the previously proposed methylcellulose or polyvinylpyrrolidone coatings. A sample of methylcellulose used by Dr. Kaufman as the basis for his publications was obtained from him. Tests showed that this material "beaded up" and exposed edges of the lens. It also dissolved too quickly. A polyvinylpyrrolidone coated lens was submerged in approximately 0.2 ml of water simulating a surgical site. Approximately 25% of PVP remained after 30 minutes.

The polyvinyl alcohol performs exceptionally well as a coating for intraocular lenses or the like. It is hydrophilic, soluble in water, swellable upon rehydration, an excellent film former, performs well on both static touch and dynamic sliding tests on the corneal endothelium has slower dissolution rate than other materials previously reported. It also does not dehydrate in the operating room for a period of 20 minutes after it has been rehydrated, and is easily cleared from the anterior chamber of the eye through biological processes. When the PVA is submerged in a simulated anterior chamber, i.e. 0.2 ml of water, approximately 75% of the PVA remains on the lens.

Other water-soluble polymers besides polyvinyl alcohol meeting the above criteria could also be used. Examples of such other materials are hydroxypropyl methylcellulose, and hydroxypropyl cellulose which retain approximately 50% of the coating weight when submerged in a simulated ocular surgical site as explained above. In this invention, it is preferable that the coating retain at least 40% of its weight after such submersion for 30 minutes. Should different materials meeting the above criteria be used, they would still be processed through the dehydrating, sterilization, and rehydrating step to provide very convenient precoated intraocular lenses and surgical tools to the ophthalmologist.

This method could be used with anterior chamber lenses, posterior chamber lenses, and lenses which use retention means other than iris loops.

In the previous description, specific examples have been used to describe the invention. However, it is understood by those skilled in the art that certain modifications can be made to these examples without departing from the spirit and scope of the invention.

We claim:
1. A method of precoating a device having a surface likely to contact a corneal endothelium during ophthalmic surgery, comprising the steps of:
   (a) coating such surface with a liquid media containing a water-soluble adherent film forming biocompatible material; and
   (b) removing the liquid media from the surface to provide a substantially dry water-soluble film on the surface.
2. The method as set forth in claim 1, wherein the method includes the further steps of:
   (c) enclosing the precoated device in a microbial barrier package; and
   (d) sterilizing such device and package.
3. A method as set forth in claim 1, wherein the water-soluble coating is also water swellable, and the method includes the further steps of:
   (c) rehydrating the substantially dry water-soluble coating to a swollen state.
4. A method as set forth in claim 3, wherein the coating is at least twice as thick in its swollen state as it is in its substantially dry state.
5. A method as set forth in claim 4, wherein the film has a thickness in the range of 5 to 300 microns in its substantially dry state; and a thickness in the range of 10 to 1000 microns in its rehydrated swollen state.
6. A method as set forth in claim 3, wherein the rehydrating step is accomplished by submersion of the substantially dry swellable film in an aqueous bath.

7. A method as set forth in claim 6, wherein the submersion is for a period of 1 to 10 minutes.

8. The method as set forth in claim 1, wherein the liquid media is water and the water is removed by evaporative drying to provide a dehydrated coating on the surface.

9. The method as set forth in claim 8, wherein the coating is also water swellable and is subsequently rehydrated by submersion in a sterile aqueous bath.

10. The method as set forth in claim 9, wherein the sterile aqueous bath is selected from the group consisting of a saline solution and a salt solution substantially balanced to the aqueous humor of the eye.

11. The method as set forth in claim 1, wherein the precoating is performed on an intraocular lens for implantation in an anterior or posterior chamber.

12. The method as set forth in claim 11, wherein the intraocular lens has an optical section and one or more iris retention loops, and a major portion of the iris retention loops are free of said water-soluble coating.

13. The method as set forth in claim 1, wherein the coating is applied by dipping the surface to be coated into the liquid media containing the water-soluble material.

14. The method as set forth in claim 1, wherein the precoating is performed on an ophthalmic surgery tool.

15. The method as set forth in claim 1, wherein the liquid media is water and the water-soluble material is a water swellable polymer.

16. The method as set forth in claim 15, wherein the water swellable polymer is polyvinyl alcohol.

17. The method as set forth in claim 1, wherein the surface is dipped coated a plurality of times.

18. The method as set forth in claim 1, wherein the coating has a dissolution rate sufficiently slow so that at least 40% of the coating is maintained on the device when submerged 30 minutes in an aqueous media at room temperature that has a volume simulating an anterior chamber.

19. A method of preparing for ophthalmic surgery, a device having a substantially dry water swellable adherent film forming biocompatible coating on a surface of the device likely to contact a corneal endothelium, comprising the steps of:
 (a) subjecting the device to an aqueous environment immediately prior to surgery to swell the coating into a soft cushion firmly adhering to the device, which cushion is sluffable; and
 (b) removing the device from the aqueous environment for use in such surgery.

20. The method as set forth in claim 19, wherein the device is submerged in a sterile aqueous bath for 1 to 10 minutes to swell the coating.

21. The method as set forth in claim 19, wherein the water swellable material is polyvinyl alcohol.

22. A method of making a device selected from the group consisting of an intraocular lens and an ophthalmic surgery tool, comprising the steps of:
 (a) forming the device;
 (b) precoating at least a portion of the device with a water-soluble and water swellable adherent film forming biocompatible coating material dissolved in an aqueous media;
 (c) dehydrating the precoated device to remove the aqueous media, and providing a substantially dry coating of the material on the device;
 (d) enclosing the precoated device in a microbial barrier package;
 (e) sterilizing the package and enclosed precoated device;
 (f) removing the sterile precoated device from the package; and
 (g) rehydrating the substantially dry film by subjecting the film to an aqueous environment immediately prior to surgery.

23. The method as set forth in claim 22, wherein the device is dip coated in an aqueous solution of polyvinyl alcohol, with the polyvinyl alcohol having a concentration of 1% to 60%.

* * * * *